(12) United States Patent
Garg et al.

(10) Patent No.: US 10,105,620 B2
(45) Date of Patent: Oct. 23, 2018

(54) PROCESS FOR SIMULTANEOUS PRODUCTION OF BENZENE LEAN GASOLINE AND HIGH PURITY BENZENE FROM CRACKED GASOLINE FRACTION

(71) Applicant: COUNCIL OF SCIENTIFIC & INDUSTRIAL RESEARCH, New Delhi (IN)

(72) Inventors: Madhukar Onkarnath Garg, Uttrakhand (IN); Prasenjit Ghosh, Uttrakhand (IN); Sunil Kumar, Uttrakhand (IN); Shrikant Madhusudan Nanoti, Uttrakhand (IN); Bhagat Ram Nautiyal, Uttrakhand (IN)

(73) Assignee: Council of Scientific & Industrial Research, New Delhi (IN)

( * ) Notice: Subject to any disclaimer, the term of this patent is extended or adjusted under 35 U.S.C. 154(b) by 153 days.

(21) Appl. No.: 15/085,582

(22) Filed: Mar. 30, 2016

(65) Prior Publication Data

US 2016/0288014 A1  Oct. 6, 2016

(30) Foreign Application Priority Data

Mar. 30, 2015  (IN) ............................ 0871/DEL/2015

(51) Int. Cl.
*B01D 3/40* (2006.01)
*B01D 3/10* (2006.01)
(Continued)

(52) U.S. Cl.
CPC ............... *B01D 3/40* (2013.01); *B01D 3/007* (2013.01); *B01D 3/10* (2013.01); *C07C 7/08* (2013.01);
(Continued)

(58) Field of Classification Search
CPC . B01D 3/007; B01D 3/10; B01D 3/40; C10G 53/06; C10G 55/06; C10G 21/20; C10G 21/28; C07C 7/08
See application file for complete search history.

(56) References Cited

U.S. PATENT DOCUMENTS

| 8,722,952 B2 * | 5/2014 | Garg | ...................... | C10G 21/28 208/313 |
| 2014/0042059 A1 * | 2/2014 | Garg | ...................... | C10G 21/28 208/289 |

* cited by examiner

*Primary Examiner* — Brian A McCaig
(74) *Attorney, Agent, or Firm* — McDonnell Boehnen Hulbert & Berghoff LLP

(57) ABSTRACT

Disclosed is a process for simultaneous production of benzene lean gasoline and recovery of high purity aromatics from narrow boiling light cracked gasoline fractions. The present invention provides a vacuum based two stage extractive distillation process, with pure NMP, for production of benzene lean gasoline (benzene content less than 0.4 Weight %) by recovery of high purity aromatics (purity more than 99 Weight %) from cracked gasoline fractions (boiling in the range of 40-90° C.) comprising benzene in the range of 10-30 weight % and close-boiling non-aromatic hydrocarbons like paraffins, iso-paraffins, olefins, di-olefins (including conjugated di-olefins), and naphthenes in the range of 70-90 weight % along with impurities containing but not limited to oxygenates, metals, chlorides, sulphur compounds, nitrogen compounds and organic peroxides.

The present invention provides an improved extractive distillation process for simultaneous production of benzene lean gasoline and benzene rich product from cracked gasoline fraction, with higher recovery of better quality products along with lower utility requirements and investment costs.

9 Claims, 2 Drawing Sheets

(51) Int. Cl.
*C10G 53/06* (2006.01)
*C10G 55/06* (2006.01)
*C10G 21/20* (2006.01)
*C10G 21/28* (2006.01)
*C07C 7/08* (2006.01)
*B01D 3/00* (2006.01)

(52) U.S. Cl.
CPC ............. *C10G 21/20* (2013.01); *C10G 21/28* (2013.01); *C10G 53/06* (2013.01); *C10G 55/06* (2013.01); C10G 2400/02 (2013.01); C10G 2400/30 (2013.01)

PROCESS FOR SIMULTANEOUS PRODUCTION OF BENZENE LEAN GASOLINE AND HIGH PURITY BENZENE FROM CRACKED GASOLINE FRACTION

CROSS-REFERENCE TO RELATED APPLICATION

This application claims priority to India patent application no. 0871/DEL/2015, dated Mar. 30, 2015, the disclosure of which is hereby incorporated by reference in its entirety.

FIELD OF THE INVENTION

The present invention relates to a process for simultaneous production of benzene lean gasoline and recovery of high purity aromatics from narrow boiling light cracked gasoline fractions.

Particularly, the present invention relates to a vacuum based two stage extractive distillation process, with pure NMP, for production of benzene lean gasoline (benzene content less than 0.4 Weight %) by recovery of high purity aromatics (purity more than 99 Weight %) from cracked gasoline fractions (boiling in the range of 40-90° C.) comprising benzene in the range of 10-30 weight % and close-boiling non-aromatic hydrocarbons like paraffins, iso-paraffins, olefins, di-olefins (including conjugated di-olefins), and naphthenes in the range of 70-90 weight % along with impurities containing but not limited to oxygenates, metals, chlorides, sulphur compounds, nitrogen compounds and organic peroxides.

More particularly, the present invention relates to an improved extractive distillation process for simultaneous production of benzene lean gasoline and benzene rich product from cracked gasoline fraction, with higher recovery of better quality products along with lower utility requirements and investment costs.

BACKGROUND OF THE INVENTION

Benzene is a toxic carcinogenic chemical. Benzene concentration in gasoline blends is placed under many environmental regulations worldwide. The Mobile Source Air Toxics (MSAT) II regulations that became effective from Jan. 1, 2011 restricts the annual average benzene level in gasoline sold in US to 0.62% vol. Typically reformate, hydrogenated pyrolysis gasoline (PG) and catalytically cracked gasoline are the main contributors of benzene in the gasoline pool.

Contrary to this, Benzene is also used extensively as an intermediate to make a variety of industrial chemicals. About 80% of benzene is consumed in the production of three chemicals, ethylbenzene, cumene, and cyclohexane. Its most widely produced derivative is ethylbenzene, precursor to styrene, which is used to make polymers and plastics. Cumene is converted phenol for resins and adhesives. Cyclohexane is used in the manufacture of Nylon. Smaller amounts of benzene are used to make some types of rubbers, lubricants, dyes, detergents, drugs, explosives, and pesticides.

FCC Gasoline as an Alternative Feedstock for Benzene Production

Currently FCC gasoline comprises nearly 10-20% of the gasoline pool in a typical refinery. In the near future with increase in demand for lighter fuels, polymer industry precursors like ethylene and propylene, FCCs will be run at higher severities so as to extract the most from heavy residuals and gas oils. High-severity FCC is thus intended to increase olefin yields. Propylene yields can be increased from 3-5% in conventional FCC to 15-28% in the high-severity process. In a high-severity FCC operation, the aromatic content of cracked naphtha is also increased to the level of 50-70% but this contains significant amounts of thiophenic sulphur impurities and is high in olefin content.

Full range FCC gasoline contains around 15-30 vol. % aromatics with up to 2 vol. % benzene and 1000-2000 ppm sulfur. A narrow C6 heart cut fraction of the full range gasoline will contain anywhere between 11-19 wt. % benzene and up to 500 ppm sulfur. So it becomes crucial to establish technologies not only to process the FCC gasoline for efficient recovery of high value materials (like benzene) but also to render it market ready (in terms of low sulfur and benzene content).

Recovery of benzene from FCC gasoline is comparatively less straight forward. The relationship of feed properties and reaction process conditions to the production of various compounds in a FCC unit is complex and thus does not present a straight forward solution for benzene control. Unlike reformate and hydrogenated PyGas, unprocessed cracked gasoline fraction (from FCC or Thermal Crackers) contain olefins along with impurities like oxygenates, metals, chlorides, sulphur compounds, nitrogen compounds, and organic peroxides. Due to the complex nature of this feedstock, an economic and reliable benzene recovery process is difficult to develop and has not been practiced in the industry so far.

Technologies being used worldwide have the sole purpose of either recovering aromatics or reducing aromatics from petroleum feedstocks like reformate, pyrolysis gasoline, or cracked gasoline fractions. There are no technologies in operation worldwide which serve the dual purpose of producing benzene lean streams from a petroleum feedstock (like the ones mentioned above), by simultaneously recovering high purity benzene.

Well known hydroprocessing routes aimed at reducing benzene from olefinic feedstocks like cracked gasoline result in saturating the olefins thus lowering the octane of the cracked gasoline fraction. Olefins in cracked gasoline contribute substantially to the octane in the gasoline pool. An attempt to reduce benzene by well-known hydro-processing routes would result in saturating the olefins as well, thus lowering the octane of the cracked gasoline fraction.

In hydrocarbon industries, aromatics like benzene, toluene, xylenes (BTX) are mainly recovered from reformate and hydrogenated pyrolysis gasoline using liquid-liquid extraction (LLE) or extractive distillation (ED) using polar aromatics selective solvents like NMP, Sulfolane, NFM, etc. There are many commercial units worldwide based on LLE and ED which are in operation and process the above mentioned feedstocks to produce BTX.

A number of patents are available which describe these processes. For example U.S. Pat. No. 3,591,490 highlights an extractive distillation process for recovery of xylenes and ethyl benzene from hydrogenated feedstocks like hydrogenated pyrolysis gasoline fraction using N-Methyl-2-Pyrrolidone (NMP) or Di-methylformamide (DMF) as a solvent. The process described comprises processing the feedstock in an extractive distillation unit followed by treating the raffinate in a washing column (a countercurrent extractor) in presence of extra circulating solvent and washing water. The solvent rich product from the extractive distillation column is then taken to a stripper column or the solvent recovery column where separation between the dissolved aromatic hydrocarbons and the solvent is affected.

Similarly U.S. Pat. No. 3,723,256 describes as process to recover BTX rich aromatic streams from a hydrotreated C6-C8 pyrolysis naphtha cut (containing about 18% non-aromatics) using a combination of pre-fractionation, extractive distillation and solvent extraction with sulfolane. U.S. Pat. No. 5,022,981 describes a solvent extraction based process for recovery of high purity aromatics from a C6-C9 feed stream. The typical feedstocks suitable for the process are; the liquid by-product stream from a pyrolysis gasoline unit after being hydrotreated or the product of a catalytic reforming unit. The solvent employed in the process is mixture of tetraethylene glycol and methoxytriglycol.

U.S. Pat. No. 7,501,549 describes a complex integrated process of benzene removal from FCC Naphtha. The main steps comprise fractionating the FCC Naphtha to obtain a benzene concentrate stream. The benzene concentrate stream is subjected to etherification over a catalyst to convert C6 Iso-olefins in the feed to corresponding ethers. This is followed by fractionation to separate the ethers from the remaining C6 fraction stream. The remaining C6 stream is then hydrotreated and can then be processed in a solvent extraction unit using Triethylene Glycol or Sulfolane.

U.S. Pat. No. 8,143,466 highlights a process for removal of benzene from reformate FCC gasoline, coker pentane/hexane, coker naphtha, FCC naphtha, straight run gasoline, pyrolysis gasoline, coal oven naphtha, and mixtures containing two or more of these streams. The benzene removal is affected by alkylation of the benzene rich feedstock wherein the benzene in feed is catalytically alkylated with alcohol and ethers to higher aromatics like toluene in a reactive distillation column and the products are separated.

U.S. Pat. No. 8,722,952 B2 elaborates an extractive distillation process scheme for production of benzene lean Gasoline by recovery of high purity benzene from unprocessed cracked gasoline fraction containing organic peroxides. The invention incorporates an intricate process involving NMP+Water solvent system. All the columns (Extractive Distillation Column, Raffinate Section Stripper, Solvent Recovery Column, and Extract Section Stripper) of the process operate above atmospheric pressure. Benzene recovery in the final extract product is more than 99% of the feed benzene with a purity of more than 97 wt. %. The simultaneous benzene content in the US Grade Gasoline obtained as the raffinate is <0.4 wt. %. The total hot and cold utility requirement for the process (for 70 tph feed throughput) is about 23.76 MMKCal/hr and 25.73 MMKCal/hr respectively.

Any process for simultaneous production of high purity benzene and US Grade Gasoline from cracked gasoline fraction which can increase the purity of benzene to reduce the cost of secondary processes (which utilize benzene) with reduction in capital investment and operating cost is of great importance.

The current specification highlights an energy efficient and cost effective (vacuum based extractive distillation) improved process over the process scheme described in U.S. Pat. No. 8,722,952 B2 with same final product specifications. Improvement with respect to increase in product yields and purities, significant reduction in hot and cold utility requirement by more than 33% and 31% respectively and considerable reduction in capital investment by elimination of raffinate and extract sections strippers and associated machinery.

SUMMARY OF THE INVENTION

The present invention provides a process to improve the product yield and purity and to reduce the operating and equipment cost for production of benzene lean gasoline (benzene content less than 0.4 weights %) by recovery of high purity benzene (purity more than 98 weights %) from unprocessed cracked gasoline fraction.

In another aspect the present invention provides a simple process configuration to reduce the number of equipment required in the process.

Still another aspect of the present invention provides operating conditions of the process to reduce the utility consumption.

In still another aspect, the present invention provides operating conditions of the process to improve the purity of extract.

Accordingly the present invention provides for a vacuum based extractive distillation process for simultaneous production of high purity benzene (>99 wt. %) and benzene lean gasoline (benzene content <0.2 wt. %) from cracked gasoline fraction, comprising the steps of:

a) combining in an extractive distillation column (EDC-1) operating in vacuum/negative pressure
   i. a preheated (upto 90% vaporization in a pressure range of −0.307 kg/cm2g to −0.247 kg/cm2g) unprocessed cracked gasoline fraction (boiling in the range of 45-95° C.) consisting of benzene concentrated unprocessed catalytically cracked gasoline fraction obtained from a fluidized catalytic cracking unit without any pre-treatment, wherein the gasoline fraction contains impurities, 10-30 weight % benzene and 70-90 weight % close-boiling non-aromatic hydrocarbons and the impurities comprise one or more of metals at a level not exceeding in ppb level, 1-400 ppm oxygenates, 0.1-3 ppm chlorides, 100-700 ppm sulphur, 0.6-14 ppm nitrogen and organic peroxides at a peroxide level of 20-50 millimoles/liter; and
   ii. pure N-Methyl-2-Pyrrolidone (NMP) at a solvent mixture to feed material weight ratio of about 2 to about 6, and wherein the feed material is introduced into the first ED column (EDC-1) below the middle section and the solvent at about 65° C.-95° C. is introduced into the column near the top section;

b) operating the EDC-1 of step (a) under vacuum and maintaining reboiler temperature in a range of 175° C. to 185° C. to obtain vapour product from top and aromatics laden solvent rich extract from the bottom;

c) cooling the vapor product from EDC-1 top as obtained in step (b), at a temperature in the range of 65° C.-75° C. and then taking it to the middle section of a second refluxed extractive distillation column (EDC-2);

d) operating the EDC-2 of step (c) under vacuum/negative pressure and maintaining the EDC-2 reboiler temperature in a range of 67° C.-80° C. to recover a raffinate phase containing gasoline having a benzene content of less than 0.2 weight % from top of EDC-2 and an extract phase containing aromatic hydrocarbons and solvent mixture from bottom of EDC-2 e) recycling the extract phase as obtained in step (d) to the top of EDC-1 to serve as reflux for EDC-1;

f) separating the solvent mixture from the extract phase as obtained in step (b) in a refluxed Solvent Recovery Column (SRC), operating under vacuum/negative pressure without using any stripping steam or water, to obtain hydrocarbon free solvent from the bottom and benzene rich extract product from the SRC top.

In an embodiment of present invention, the hot solvent, free from hydrocarbons, is separated at the SRC bottom and is recycled back to the EDC-1 after utilization of its heat in the EDC-1 side reboiler, EDC-2 reboiler and the main FCC gasoline feed pre-heater in the said order and finally cooled in the solvent cooler to about 65° C.-95° C. prior to its entry in EDC-1. In another embodiment of present invention, the top pressure of EDC-1, EDC-2 and SRC is maintained at a pressure of −0.39 to −0.19 kg/cm2g; −0.59 to −0.39 kg/cm2g and −0.62 to −0.42 kg/cm2g respectively.

In yet another embodiment of present invention, the weight ratio of reflux to the raffinate phase from the EDC-2 top is 0.1:1 to 0.5:1.

In still another embodiment of present invention the ratio of recycle to EDC-1 and the final dearomatized raffinate product is 0.1:1 to 0.15:1.

In still another embodiment of present invention the reflux ratio in the Solvent Recovery Column is in the range 3.5 to 4.5 wt./wt. and the column reboiler temperature is in the range 175° C.-187° C. at the operating pressure.

In still another embodiment, present invention provides greater than 99 weight % of the benzene present in the catalytically cracked gasoline feed is recovered in the final aromatics rich extract product from SRC top.

In still another embodiment of present invention the purity of benzene in the final extract is more than 99 wt. % and benzene content of the final de-aromatized FCC Gasoline product (from EDC-2 top) is less than 0.2 wt. %

In still another embodiment of present invention the said product yield and purities from the cracked gasoline feed are obtained using two coupled extractive distillation columns in series operating under vacuum in conjunction with a solvent recovery column operating under vacuum without the aid of any stripping steam or water.

In still another embodiment, the present invention provides an energy efficient process with more than 33% heating utility savings and more than 30% cold utility savings, wherein no Raffinate and Extract Section Strippers or wash columns for final product purification are required thus reducing the overall plant capex and installation cost of the process.

BRIEF DESCRIPTION OF THE DRAWINGS

FIG. 1 graphically illustrates the extractive distillation process according to the present invention using pure NMP solvent. The feed, unprocessed catalytically cracked gasoline fraction (boiling in the range 40° C.-90° C.) containing a mixture of benzene, olefins, di-olefins (including conjugated di-olefins), non-aromatic hydrocarbons like naphthenes, paraffins, iso-paraffins along with impurities like oxygenates, metals, chlorides, sulphur compounds, nitrogen compounds and organic peroxides is introduced through line 1-A below the middle portion of a multi-stage ED column C-01 after pre-heating in Feed pre-heater E-01 which is using circulating solvent as the hot stream 9-B.

The ED column C-01 overhead product is passed through line 2 and is condensed in the cooler E-02 to about 70° C. to yield a mixed vapor-liquid overhead stream 2-A which is the fed to the middle section of the second ED column C-02. C-02 is a refluxed ED column. The solvent along with dissolved hydrocarbons in the feed to C-02 is withdrawn as product from the bottom reboiler. Adequate reflux in C-02 minimizes any solvent carryover to the top product. The ED column C-02 overhead product enriched in olefins and non-aromatic hydrocarbon(s) and lean in benzene is passed through line 4 and is condensed in cooler E-03 and is collected in the overhead drum V-01. A portion of the condensed hydrocarbon from V-01 can be returned to ED column C-02 as reflux through line 6-A, while the benzene lean gasoline product can be routed either to gasoline storage or to other processing units through line 6.

The bottom product from C-02 is recycled back to the top of C-01 as a reflux stream (line 5/5-A). The reboiler of C-02 (at a temperature of 65-75° C.) is run using the hot circulating solvent through 9-A/9-E. Both the sequential ED columns C-01 and C-02 are maintained in vacuum at a pressure below atmospheric pressure (−0.289 KG/cm2g and −0.489 Kg/cm2g top pressure respectively).

The bottom stream 3 from ED column C-01 is fed to another distillation column C-03 (usually referred as Solvent Recovery Column (SRC)) near the middle of the column. The SRC overhead stream 7 is condensed in condenser E-06 and routed to overhead drum V-02 through line 7-A. A portion of benzene rich extract from overhead drum V-02 can be returned through line 8-A as reflux for column C-03 and rest can be routed to storage as Extract (product), i.e., benzene of high purity, through line 8 or to any other processing unit. Since the solvent used is pure NMP, in order to maintain low reboiler temperatures the SRC column is also operated at a pressure below normal atmospheric pressure (−0.517 kg/cm2g top pressure).

Hot Circulating solvent stream 9 (at ~180° C.) from solvent recovery column (C-03) bottom is routed to C-01 side reboiler E-08 (near stage 40), the C-02 reboiler E-05, Feed-Lean solvent heat exchanger (E-01) through line 9-B and solvent cooler E-09 (as in Examples 2 and 3). The hot circulating solvent from C-03 bottom may also bypass the E-08 (as in Example 1) and directly be routed to C-02 reboiler through line 9-E.

Finally this circulating solvent, at around 70-90° C., after exchanging heat is fed to ED column C-01 through line 9-D near the top of the column below the reflux (stream 5-A) entry location.

E-04, E-05, E-07 are the reboilers of column C-01, C-02, and C-03 respectively.

Figure 1:
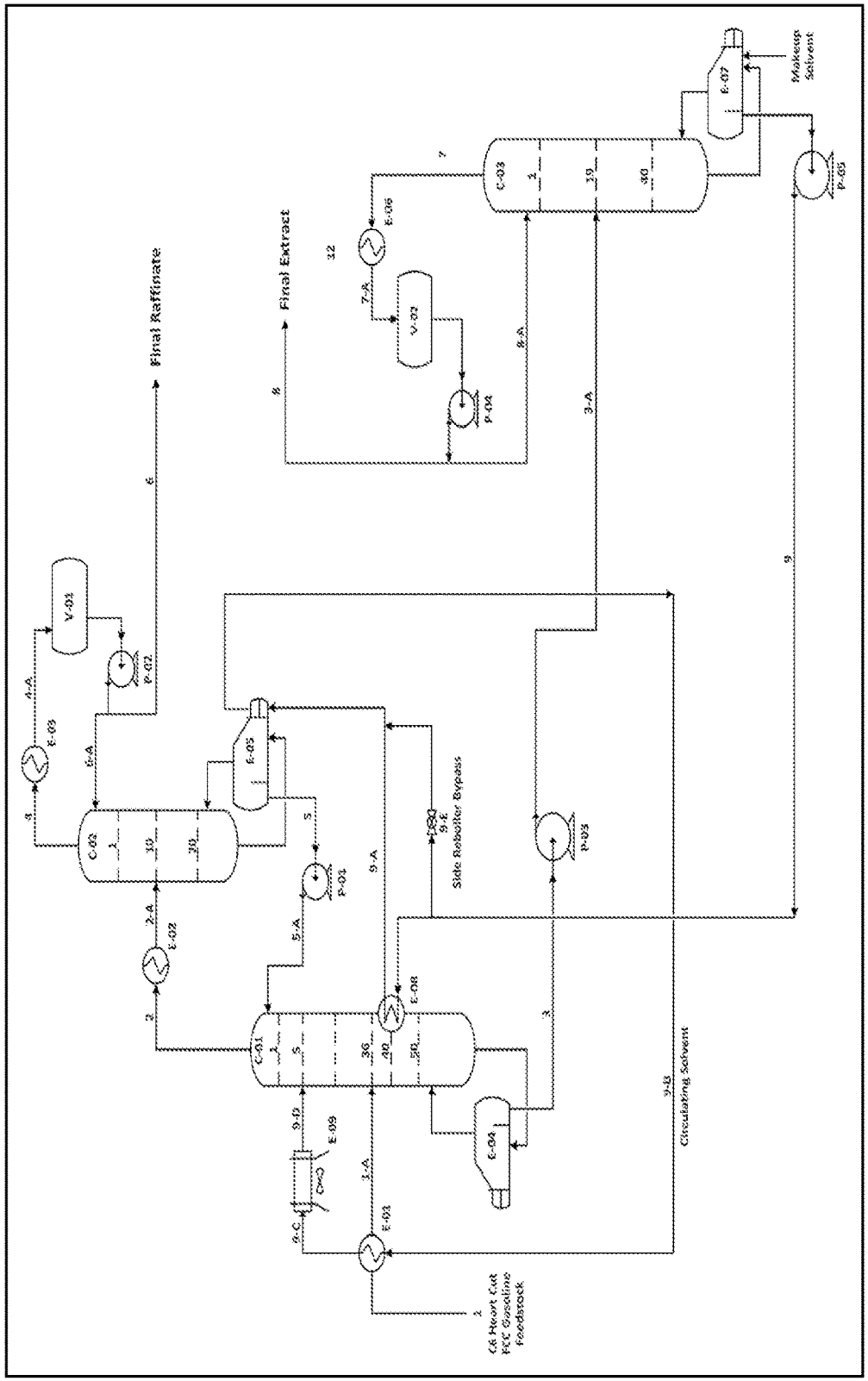
FIG. 1 is a schematic representation of the improved process of the invention with Pure NMP Solvent.
Figure 2:
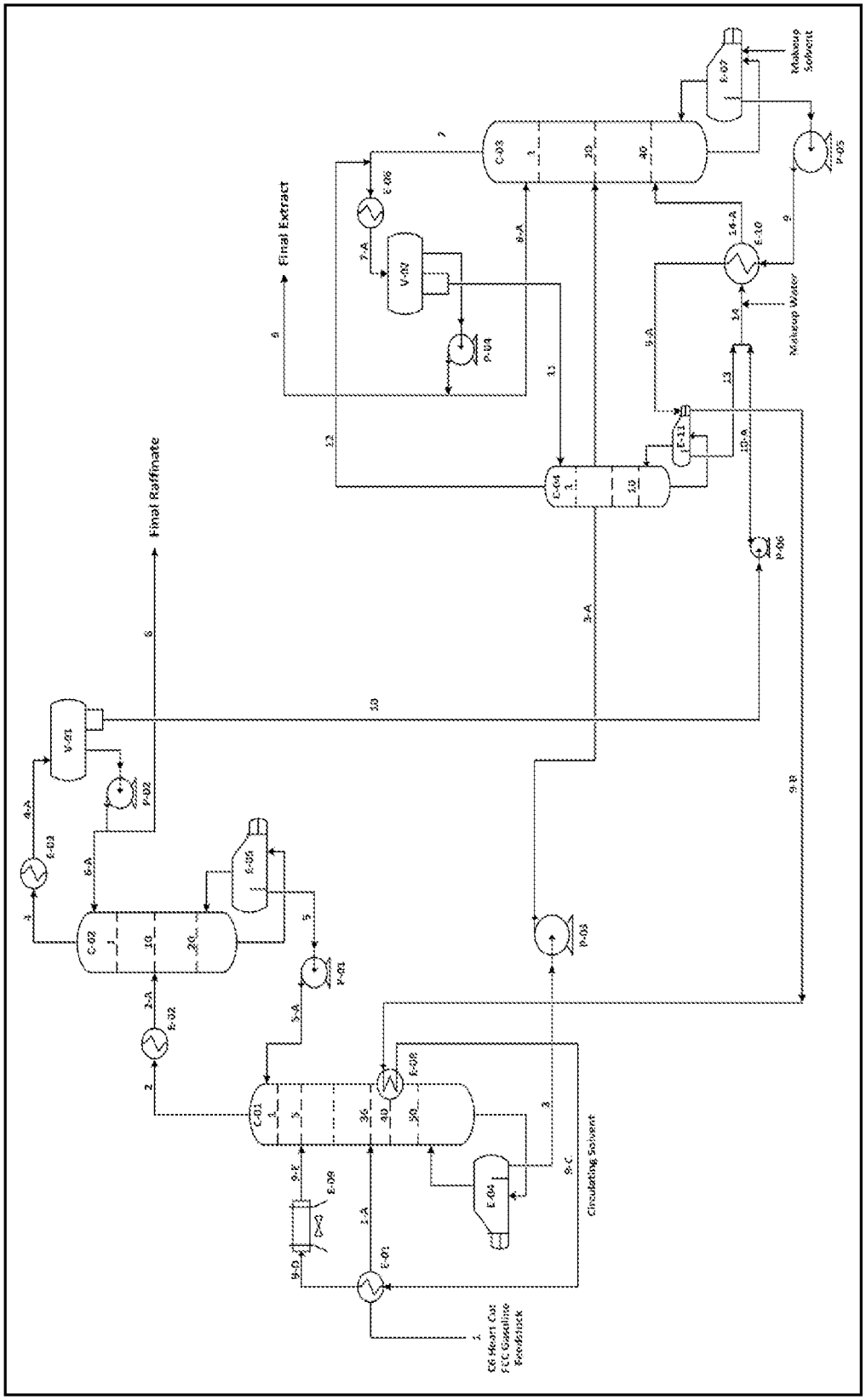

FIG. 2 is a schematic representation of a Comparative 2 Stage Positive Pressure based Extractive Distillation with Aqueous NMP Solvent. FIG. 2 graphically illustrates the extractive distillation scheme if instead of pure NMP, NMP+Water is used as the solvent system in the scheme of FIG. 1 and the ED columns (C-01, C-02) are operated at positive pressure (pressures above atmospheric pressure). With addition of water in the solvent, the overhead vessels of the ED columns need to be modified in order to facilitate separation and collection of water carried along with the hydrocarbons to the top. An extra water heater also needs to be added in order to provide stripping steam for the solvent recovery column. In order to reduce loss of extract hydrocarbons an extract water stripper is also added. This scheme has been used just for a comparison (Example 4) with the main scheme highlighted in FIG. 1 and no result of it is claimed or should be construed as an improvement (which is the main essence of the current patent) over the previous U.S. Pat. No. 8,722,952 B2 (by the same inventors).

The description for FIG. 2 is similar to that of FIG. 1 with the exception that the solvent system is NMP+Water, a water heater (E-10) and an extract water stripper C-04 has been used in this modified scheme and all the columns are operated at positive pressure (pressure above normal atmospheric pressure).

The feed, benzene concentrated unprocessed catalytically cracked gasoline fraction (boiling in the range 40° C.-90° C.) containing a mixture of benzene, olefins, di-olefins (including conjugated di-olefins), non-aromatic hydrocarbons like naphthenes, paraffins, iso-paraffins along with impurities like oxygenates, metals, chlorides, sulphur compounds, nitrogen compounds and organic peroxides is introduced through line 1-A below the middle portion of a multi-stage ED column C-01 through Feed pre-heater E-01 which is using circulating solvent as the hot stream 9-C.

The ED column C-01 overhead product is passed through line 2 and is condensed in the cooler E-02 to about 70° C. to yield a mixed vapor-liquid overhead stream 2-A which is the fed to the middle section of the second ED column C-02. C-02 is a refluxed ED column. The solvent along with dissolved hydrocarbons in the feed to C-02 is withdrawn as product from the bottom reboiler. Adequate reflux in C-02 minimizes any solvent carryover to the top product. The ED column C-02 overhead product enriched in olefins and non-aromatic hydrocarbon(s) and lean in benzene is passed through line 4 and is condensed in cooler E-03 and is collected in the overhead drum V-01. Due to presence of water in the main solvent system an extra water stream is separated out in V-01 which is recovered from boot of V-01 and then pumped (using P-06) to the water heater E-10. A portion of the condensed hydrocarbon from V-01 can be returned to ED column C-02 as reflux through line 6-A, while the benzene lean gasoline product can be routed either to gasoline storage or to other processing units through line 6.

The bottom product from C-02 is recycled back to the top of C-01 as a reflux stream (line 5/5-A). The reboiler of C-02 (at a temperature of 75-80° C.) is run using a hot utility like MP steam. Both the sequential ED columns C-01 and C-02 are maintained in vacuum at a pressure above atmospheric pressure (0.517 KG/cm2g and 0.207 Kg/cm2g top pressure respectively).

The bottom stream 3 from ED column C-01 is fed to another distillation column C-03 (usually referred as Solvent Recovery Column (SRC)) near the middle of the column. This SRC overhead stream 7 is condensed in condenser E-06 and routed to overhead drum V-02 through line 7-A. A portion of benzene rich extract from overhead drum V-02 can be returned through line 8-A as reflux for column C-03 and rest can be routed to storage as Extract (product), i.e., benzene of high purity, through line 8 or to any other processing unit. The SRC column is operated at 0.258 kg/cm2g top pressure.

The V-02 boot water containing traces of dissolved benzene rich hydrocarbons and solvent is passed to Extract Water Stripper (EWS) C-04 through line 11. The overhead stream 12, comprising mainly benzene rich hydrocarbons, from C-04 is mixed with C-03 overhead vapor stream 7 and the mixed stream is sent to the overhead condenser E-06 and the bottom stream 13, which is free of hydrocarbons and solvent, is mixed with the water stream from V-01 (line 10-A) and is taken to the water heater E-10 for production of stripping steam (line 14-A) for use in the SRC.

Hot Circulating solvent stream 9 (at ~180° C.) from solvent recovery column (C-03) bottom is first routed to the water heater E-10, then to the C-04 reboiler E-011, then to the C-01 side reboiler E-08 (near stage 40), followed by Feed-Lean solvent heat exchanger (E-01) through line 9-C and finally to the solvent cooler E-09.

Finally this circulating solvent, at about ~90° C., after exchanging heat is fed to ED column C-01 through line 9-E near the top of the column below the reflux (stream 5-A) entry location.

E-04, E-05, E-07 are the reboilers of column C-01, C-02, and C-03 respectively and run on a hot utility like MP Steam.

DETAILED DESCRIPTION OF THE INVENTION

The present invention (as depicted in FIG. 1) highlights a vacuum based two stage extractive distillation process for the production of benzene lean gasoline (benzene content less than 0.4 weight %) by recovery of high purity benzene (purity more than 98 weight %) from unprocessed cracked gasoline fractions. The said gasoline fraction is obtained (without any pre-treatment) from a Fluidized Catalytic Cracking (FCC) unit of a petroleum refinery. The said unprocessed cracked gasoline fraction, comprises of benzene and close-boiling non-aromatic hydrocarbons like paraffins, iso-paraffins, olefins, di-olefins (including conjugated di-olefins), and naphthenes along with impurities containing but not limited to oxygenates, metals, chlorides, sulphur compounds, nitrogen compounds, and organic peroxides.

The unprocessed cracked gasoline fraction used in this invention should preferably have a boiling range of 40° C. to about 90° C.

Preferably, the benzene content in the feed can be about 5 to 40 weight % (more preferably about 10-30 weight %), and the corresponding non-aromatic hydrocarbon content is about 60-95 weight % (more preferably about 70-90 weight %).

In the current invention a better and energy efficient two stage vacuum based extractive distillation process is provided using one of the solvents (reported by us in U.S. Pat. No. 8,722,952 B2) which remains thermally and oxidatively stable for production of US Grade gasoline (Bz. <0.4 wt. %) by recovery of high purity benzene (purity >98 wt. %) from cracked gasoline like FCC C6 Heart Cut Naphtha. In our current invention we are using pure NMP without any co-solvent.

The composition of the said cracked gasoline fraction used in the process development is given in Table 1.

TABLE 1

Characteristics of unprocessed catalytically cracked gasoline fraction (Feed)

| | FEED CHARACTERIZATION | ° C. |
|---|---|---|
| | Distillation, ASTM, D86, % Vol. | |
| 1 | Initial boiling point (IBP) | 48.0 |
| | 5% | 67.2 |
| | 10% | 67.5 |
| | 20% | 67.6 |
| | 30% | 68.0 |
| | 40% | 68.3 |
| | 50% | 68.6 |
| | 60% | 69.3 |
| | 70% | 69.9 |
| | 80% | 70.9 |
| | 90% | 72.6 |
| | 95% | 74.6 |
| | Final boiling point (FBP) | 91.8 |
| | Distillate (ml) | 98.00 |
| | Losses (ml) | 0.80 |
| | Residue (ml) | 1.20 |
| | Class type analysis GC, weight % | |
| 2 | Mono Olefins | 35.72 |
| | C5-C6 Di-olefins | 1.18 |
| | Paraffins (Nor + Iso) | 31.54 |
| | Naphthenes | 17.47 |
| | Aromatics (Benzene) | 14.09 |
| 3 | Total Sulfur, ppm | 108.10 |
| 4 | Total oxygenates (EN-13132), ppm | 208.00 |
| 5 | Total Nitrogen, ppm | 6.65 |
| 6 | Total Chlorides, ppm | 0.10 |

TABLE 1-continued

Characteristics of unprocessed catalytically cracked gasoline fraction (Feed)

| | FEED CHARACTERIZATION | ° C. |
|---|---|---|
| 7 | Metals, ppb | 40.00 |
| 8 | Peroxide Value, milimoles/litre | 36.75 |
| 9 | Density kg/m$^3$, @ 20° C. | 725.00 |
| 10 | Research Octane Number (RON) | 87.00 |

As seen in Table 1, the said cracked gasoline fraction contains olefins along with other hydrocarbons and impurities like sulfur, oxygenates, chlorides, metals, organic peroxides etc. and boils in a narrow range of 40° C. to 90° C. Total aromatics in the feedstock is 13.71 wt. % with 13.16 wt. % benzene, remaining being toluene.

In this process pure aromatic selective solvent NMP and pre-heated (upto 90% vaporization at a pressure of around −0.247 kg/cm2g) unprocessed cracked gasoline fraction in the weight ratio ranging from 2.0 to 6.0, more preferably 3.0 to 4.0, are treated in an Extractive Distillation column (first in the sequence) maintained at a negative pressure (pressure below normal atmospheric pressure, −0.285 kg/cm2g top pressure) wherein the unprocessed cracked gasoline fraction enters the first ED column below the middle section and solvent enters the column near the top section below the reflux entry point. Re-boiler temperature of the first ED column (EDC-1) is maintained in the range 170° C. to 180° C.

Vapor product recovered from top of EDC-1 is cooled to around 70° C. and then sent into a second ED column (EDC-2), near its middle section, which is also maintained at a negative pressure (−0.489 kg/cm2g top pressure) while bottom product from EDC-1 is the benzene loaded solvent (Extract Phase) which is sent to the downstream solvent recovery unit.

Vapor product from EDC-1 top contains hydrocarbons along with the solvent NMP. A low reboiler temperature (67° C.-80° C.) is maintained in EDC-2 which helps in recovery and separation of the high boiling solvent from the light hydrocarbons. Adequate reflux (wt./wt. reflux ratio of 0.1:1-0.5:1) in EDC-2 prevents carryover of solvent to the benzene lean (Bz. <0.4 wt. %) top raffinate product. The bottom reboiler product of EDC-2 (solvent and some dissolved hydrocarbons) is recycled back to the top of EDC-1 as reflux.

Together the EDC-1 and EDC-2 form a closed process loop and help in recovery of high purity benzene (purity >98 wt. %) from the FCC gasoline feedstock with minimal loss in yield of Bz. lean gasoline (Bz. <0.2 wt. %).

The final raffinate product obtained from top of EDC-2 is practically free of the solvent (NMP <22 ppm) and does not require any further water washing. The raffinate obtained containing negligible benzene (<0.2 wt. %) can be directly sent for storage or to any other downstream refinery unit.

Separation of the solvent from the Extract Phase is accomplished in a Solvent Recovery Column (SRC) to obtain hydrocarbon free solvent from the bottom and benzene (with purity more than 98 wt %) from the SRC top. The solvent recovery column is also operated in vacuum (−0.517 kg/cm2g top pressure). Adequate reflux is provided in the SRC (reflux ratio of 3.5-4.0) to minimize solvent carryover to the top. Solvent content of the final aromatics rich extract hydrocarbon product from SRC top is <25 ppm.

In the process, recovery of the benzene is more than 99 weight % (based on benzene content of unprocessed cracked gasoline) along with purity of more than 98 weight %.

In order to make the process more energy efficient, the hot solvent from the SRC bottom is used to run the EDC-1 side reboiler, EDC-2 reboiler and pre-heat the FCC gasoline feedstock to upto 90% vaporization. After pre-heating the feedstock the circulating solvent is cooled only upto 70° C. before introducing it into EDC-1 near the top.

Current invention provides a process with considerable lower hot utility requirement, 15.94 MMKCal/hr as against to ~23.76 MMKCal/hr disclosed in U.S. Pat. No. 8,722,952 B2 for same feed throughput, without using the Raffinate and Extract Section Strippers (described in U.S. Pat. No. 8,722,952 B2) with improved benzene purity and improved yield of gasoline.

EXAMPLES

The following examples are given by way of illustration and therefore should not be construed to limit the scope of the invention.

The feedstock used in these examples is benzene concentrated unprocessed catalytically cracked gasoline fraction (boiling in the range 48° C.-91.8° C.) as described in Table 1.

In Example 1, comparison of experimental data (given in U.S. Pat. No. 8,722,952 B2) and simulation predicted results are shown to validate component interaction parameters to be used in the simulation studies described in the examples 2, 3, 4, 5 and 6 of the present invention.

In Example 2, the process described in FIG. 3 of U.S. Pat. No. 8,722,952 B2 has been simulated and the corresponding results have been presented. These results will help in quantitatively comparing the current energy efficient and cost effective (vacuum based extractive distillation) improved process scheme with the process scheme in U.S. Pat. No. 8,722,952 B2.

In Example 3, the process described in FIG. 2 of the current invention has been simulated and the corresponding results have been presented. Simulation results of this case will show the disadvantage of using positive pressures in the columns and using water as a co-solvent along with NMP in comparison to the current invention as illustrated in FIG. 1.

In Example 4, 5 and 6, results are shown for the process scheme depicted in FIG. 1 of current invention. In all these cases all columns are maintained at negative pressure and the main solvent system is pure NMP.

Feedstock used for all the examples is FCC Gasoline C6 heart Cut Naphtha as described in Table 1. Feed flow rate of 70 tph and S/F ratio of 4.0 in the main Extractive Distillation column has been kept constant for all the Examples 2 to 6.

Example 1: For Fine Tuning Component Interaction Parameters

Experimental ED column run with NMP+Water (97.8:2.2) wt. % described in Table 4 of U.S. Pat. No. 8,722,952 B2 has been used for fine tuning component interaction parameters which were used in the simulation cases described in Examples 2, 3, 4, 5 and 6 of the current invention.

A simple extractive distillation model similar to the one used for experimentation in the lab was developed in a commercial process simulator. Typical column operating parameters in the simulation model like (number of stages, reflux ratios, hydrocarbon feed, solvent, column top and bottom product flow rates, etc) were kept same as that maintained during the lab run.

The component interaction parameters were rigorously fine tuned so that the product profiles (flow rates and compositions) of the simulation model matched the corresponding values obtained during the experimental run.

The following column operating parameters have been reported in Table 4 of U.S. Pat. No. 8,722,952 B2.

Feed: Catalytically unprocessed cracked gasoline fraction, as per detail composition given in Table 1
Solvent: Mixture of NMP and water (97.8:2.2) wt. %
Solvent-to-feed weight ratio of 3.55
Reflux ratio 0.6 v/v.
Column Top Pressure—0.93 atm, Column Bottom Pressure—0.96 atm
Column Reboiler Temp. —160° C.

TABLE 2

Comparison of Experimental and Simulation Results

|  | Feed Mass % | Raffinate (Solvent Free) Mass % | | Extract (Solvent Free) Mass % | |
| --- | --- | --- | --- | --- | --- |
| Components |  | Experimental | Simulation | Experimental | Simulation |
| Mono Olefins | 35.72 | 41.20 | 41.68 | 0.40 | 0.33 |
| C6 Di-Olefins | 1.18 | 0.42 | 1.11 | 1.43 | 1.60 |
| Paraffins (Normal + Iso) | 31.54 | 38.07 | 36.80 | 0.24 | 0.32 |
| Naphthenes | 17.47 | 20.29 | 20.40 | 0.01 | 0.08 |
| Benzene | 14.09 | 0.02 | 0.02 | 97.92 | 97.67 |
| Total | 100.00 | 100.00 | 100.00 | 100.00 | 100.00 |
| Benzene Recovery in Extract | % of Feed | | | | |
| Experimental | 99.87 | | | | |
| Simulation | 99.87 | | | | |
| Reboiler Temperature | ° C. | | | | |
| Experimental | 160.00 | | | | |
| Simulation | 159.56 | | | | |

Slight variations in experimental composition of certain species like di-olefins and paraffins, is due to the inaccuracy of the measuring instrument (Gas Chromatograph) in resolving the components and also due to material loss during sample collection, whereas results obtained by simulation will be free from material balance errors.

Results in the Table 2 indicate a close match between the phase compositions obtained using the simulation model and experimental runs.

The fine tuned component interaction parameters were thus used for simulating the various cases as described in the following Examples 2, 3, 4, 5 and 6.

Example 2: Simulation Results of the Base Case

In this example, simulation results of the process illustrated in FIG. 3 of the previous patent (U.S. Pat. No. 8,722,952 B2) are presented.

Referring to FIG. 3 of U.S. Pat. No. 8,722,952 B2; ED Run with NMP and Water (97.8:2.2) wt. % (With side reboiler at Stage 55 in Col. 1)

Main ED Column operating pressure (Top pressure—0.031 Kg/cm2g)
Solvent Recovery Column operating pressure (Top pressure—0.207 Kg/cm2g)
Hydrocarbon Feed: Benzene concentrated unprocessed catalytically cracked gasoline fraction (boiling in the range 48° C.-92° C.) as described in Table 1 with a flow rate of 70 tph
Solvent System: Mixture of NMP and Water (97.8:2.2) wt. %
Solvent Entry Temperature in Main ED Column: 60° C.
Hydrocarbon Feed to Main ED column vapor fraction: 0.8 at 0.288 kg/cm2g
Process Flow Scheme as in FIG. 3 of U.S. Pat. No. 8,722,952 B2
Solvent System to Feed Wt. Ratio in main ED column—4.0:1.0
ED Column/Solvent Recovery Column Stage Efficiency—0.45

TABLE 3-A

Column Operational Parameters and Utility Consumption for Example 2

| Parameters | UOM | Main Extractive Distillation Column (C-01) | Solvent Recovery Column (C-03) |
| --- | --- | --- | --- |
| Total Number of Stages | Actual | 70 | 40 |
| Stage Efficiency assumed |  | 0.45 | 0.45 |

TABLE 3-A-continued

Column Operational Parameters and Utility Consumption for Example 2

| Parameters | UOM | Main Extractive Distillation Column (C-01) | Solvent Recovery Column (C-03) |
|---|---|---|---|
| Main Feed Stage Location | | 45 | 20 |
| Column Top Pressure | Kg/cm2g | 0.031 | 0.207 |
| Reboiler Temp. | ° C. | 174.58 | 181.83 |
| Reboiler Duty (1) | MMKCal/hr | 17.44 | 6.32 |
| Overhead Condenser Duty (2) | MMKCal/hr | 10.15 | 11.00 |
| Column Reflux Rate | TPH | 20.00 | 43.00 |
| Column Side Reboiler Duty | MMKCal/hr | 1.00 | — |
| Stripping Steam Required | TPH | — | 10.5 |
| Vaporization of water in Water Heater | % | | |
| Circulating Solvent Cooler Duty (3) | MMKCal/hr | 4.571 | |
| Total Heating Duty Required Σ(1) | MMKCal/hr | 23.76 | |
| Total Cooling Duty Required Σ(2) + (3) | MMKCal/hr | 25.73 | |

TABLE 3-B

Product Composition and Flow Rates for Example 2

| Components | Feed Mass % | Raffinate (Solvent Free) Mass % | Extract (Solvent Free) Mass % |
|---|---|---|---|
| Mono Olefins | 35.72 | 41.63 | 0.12 |
| C6 Di-Olefins | 1.18 | 1.12 | 1.56 |
| Paraffins (Normal + Iso) | 31.54 | 36.71 | 0.31 |
| Naphthenes | 17.47 | 20.38 | 0.01 |
| Aromatics (Benzene) | 14.09 | 0.17 | 98.00 |
| Total Flow Rate, Kg/hr | 70000.00 | 60039.74 | 9960.26 |
| Benzene recovery in Extract | % of Feed | | 98.96 |
| Benzene purity in Extract | Wt. % | | 98.00 |
| Benzene in Raffinate | Wt. % | 0.17 | |
| Raffinate yield | % of Feed | 85.77 | |

Results presented in Tables 3-A and 3-B indicate that the process illustrated FIG. 3 of U.S. Pat. No. 8,722,952 B2 produces US Grade Gasoline (<0.4 wt. % benzene) by recovering high purity benzene (purity >97.0 wt. %) from FCC C6 Heart Cut Gasoline.

The total heating duty required for the process is 23.76 MMKCal/hr and cooling duty required is 25.73 MMKCal/hr for a FCC Gasoline feed throughput of 70 tph.

Referring to the process flow diagram of FIG. 3 of U.S. Pat. No. 8,722,952 B2; the solvent recovery column C-03 requires a high amount of stripping steam (generated in E-14), 10.5 tph. A substantial amount of circulating solvent heat is thus lost in heating water for steam generation (in E-14) and is hence not available for providing heat to the ED side reboiler (E-06). Only 1.0 MMKCal/hr of heat can be provided by the hot circulating solvent in the ED side reboiler (E-06). If more heat is extracted in the side reboiler (E-06) there will not sufficient steam generation in the water heater E-14. This will eventually increase the Solvent Recovery Column (C-03) reboiler duty and hence the hot utility consumption.

Thus an energy efficient and cost effective (vacuum based extractive distillation) improved process was developed which reduces the overall hot and cold utility consumption in the process and still gives high purity products with high yields. The following examples 3, 4, 5 and 6 highlight results (product yields, purities and utility consumption) of various simulation studies for the improved process.

Example 3

ED Run with NMP and Water (97.8:2.2) wt. % (With side reboiler at Stage 40 in Col. 1)
ED Column (Col.1) operating pressure (0.517 Kg/cm2g)
Feed: Benzene concentrated unprocessed catalytically cracked gasoline fraction (boiling in the range 48° C.-91.8° C.) as described in Table 1 (90% vaporization at 0.65 kg/cm2g)
Solvent System: Mixture of NMP and Water (97.8:2.2) wt. %
Solvent Entry Temperature in Col. 1: 90° C.
Process Flow Scheme as in FIG. 2
Solvent System to Feed Wt. Ratio—4.0: 1.0
ED Column/Solvent Recovery Column Stage Efficiency—0.50
Individual Column operating parameters are provided in Table 4 as follows:

TABLE 4-A

Column Operating Parameters for Example 3 (Refer FIG. 2)

| Parameters | UOM | EDC-1 (C-01) | EDC-2 (C-02) | SRC (C-03) | EWS (C-04) |
|---|---|---|---|---|---|
| Total Number of Stages | Actual | 50 | 20 | 40 | 10 |
| Stage Efficiency assumed | | 0.5 | 0.5 | 0.5 | 0.5 |
| Main Feed Stage Location | | 36 | 10 | 20 | 1 |
| Column Top Pressure | Kg/cm2g | 0.5 | 0.1 | 0.258 | 0.5 |
| Reboiler Temperature | ° C. | 180.84 | 100.58 | 182.50 | 113.38 |
| Reboiler Duty (1) | MMKCal/hr | 15.102 | 5.920 | 4.415 | 0.550* |
| Overhead Condenser Duty (2) | MMKCal/hr | 5.058 | 8.236 | 9.487 | — |
| Column Reflux Rate (If any) | TPH | 10.00 | 20.00 | 40.00 | — |
| Column Side Reboiler Duty (If any) | MMKCal/hr | 1.5 | — | — | — |

TABLE 4-A-continued

| Column Operating Parameters for Example 3 (Refer FIG. 2) | | | | | |
|---|---|---|---|---|---|
| Parameters | UOM | EDC-1 (C-01) | EDC-2 (C-02) | SRC (C-03) | EWS (C-04) |
| Stripping Steam Required (If any) | TPH | — | — | 7.751 | — |
| Feed Pre-heater duty | MMKCal/hr | | 4.937 | | |
| Circulating Solvent Cooler Duty (3) | MMKCal/hr | | 4.471 | | |
| Total Heating Duty Required Σ(1) except* | MMKCal/hr | | 25.44 | | |
| Total Cooling Duty Required Σ(2) + (3) | MMKCal/hr | | 27.25 | | |

EDC-1: Extractive Distillation Column 1;
EDC-2: Extractive Distillation Column 2
SRC: Solvent Recovery Column;
EWS: Extract Water Stripper Product summary is provided in Table 4-B as follows:

TABLE 4-B

| Product Composition and Flow Rates for Example 3 | | | |
|---|---|---|---|
| Components | Feed Mass % | Raffinate (Solvent Free) Mass % | Extract (Solvent Free) Mass % |
| Mono Olefins | 35.72 | 42.12 | 1.63 |
| C6 Di-Olefins | 1.18 | 0.52 | 4.67 |
| Paraffins (Normal + Iso) | 31.54 | 36.50 | 5.04 |
| Naphthenes | 17.47 | 20.74 | 0.08 |
| Aromatics (Benzene) | 14.09 | 0.11 | 88.57 |
| Total Flow Rate, Kg/hr | 70000.00 | 58939.84 | 11060.16 |
| Benzene recovery in Extract | % of Feed | 99.32 | |
| Benzene purity in Extract | Wt. % | 88.57 | |
| Benzene in Raffinate | Wt. % | 0.11 | |
| Raffinate yield | % of Feed | 84.20 | |

Results presented in Tables 4-A and 4-B indicate that when the ED column (Col. 1) is operated at a positive pressure of 0.5 kg/cm2g (pressure above 1 atmosphere); the aromatics purity in the final extract is only 88.57 wt. %, the rest being non-aromatic hydrocarbons. As a result the raffinate yield also decreases. The total heating and cooling duty requirements is also very high (25.44 and 27.25 MMKCal/hr respectively). The hot circulating solvent has potential to provide only 1.5 MMKcal/hr of heat to side reboiler of the main ED column (Col. 1). Substantial amount of steam (7.751 TPH) is required in SRC to strip the benzene from solvent. As a result substantial amount of heat present in the hot circulating solvent (4.174 MMKCal/hr) is utilized in the water heater to generate this steam which otherwise would have been available for use in the Col. 1 side reboiler.

An extra column (C-04), the Extract Water Stripper, has been added in this scheme (as shown in FIG. 2) so as to ensure minimal loss of aromatics. There is also an extra water heater E-10 which is used to generate steam from the water coming from the overhead receiver V-01 and C-04 bottom.

The main process scheme of the current patent is the one described in FIG. 1. It does not contain the extra C-04 column or the water heater E-10, since no water is required in the entire process.

The following Examples 4, 5 and 6 will highlight the results of various simulation studies done on the main process scheme (as illustrated in FIG. 1 of the current patent).

Example 4

ED Run with pure NMP (Without side reboiler in Col. 1)
Main ED Column (Col.1) operating pressure (−0.285 Kg/cm2g)

Feed: Benzene concentrated unprocessed catalytically cracked gasoline fraction (boiling in the range 48° C.-91.8° C.) as described in Table 1 (90% vaporization at 0.5 kg/cm2g)

Solvent System: Pure NMP

Solvent Entry Temperature in Col. 1: 90° C.

Process Flow Scheme as in FIG. 1

Solvent System to Feed Wt. Ratio: 4.0

ED Column/Solvent Recovery Column Stage Efficiency—0.50

Individual Column operating parameters are provided in Table 5-A as follows:

TABLE 5-A

| Column Operating Parameters for Example 4 (Refer FIG. 1) | | | | |
|---|---|---|---|---|
| Parameters | UOM | EDC-1 (C-01) | EDC-2 (C-02) | SRC (C-03) |
| Total Number of Stages | Actual | 50 | 20 | 40 |
| Stage Efficiency assumed | | 0.5 | 0.5 | 0.5 |
| Main Feed Stage Location | | 36 | 10 | 20 |
| Column Top Pressure | Kg/cm2g | −0.285 | −0.489 | −0.517 |
| Reboiler Temperature | ° C. | 175.12 | 74.58 | 181.90 |
| Reboiler Duty (1) | MMKCal/hr | 12.219 | 0.652* | 5.409 |
| Overhead Condenser Duty (2) | MMKCal/hr | 1.221 | 6.306 | 4.948 |
| Column Reflux Rate (If any) | TPH | 6.00 | 12.02 | 37.55 |
| Column Side Reboiler Duty (If any) | MMKCal/hr | — | — | — |
| Stripping Steam Required (If any) | TPH | — | — | — |
| Feed Pre-heater duty | MMKCal/hr | | 4.835 | |
| Circulating Solvent Cooler Duty (3) | MMKCal/hr | | 6.978 | |
| Total Heating Duty Required Σ(1) except* | MMKCal/hr | | 17.63 | |
| Total Cooling Duty Required Σ(2) + (3) | MMKCal/hr | | 19.45 | |

Product summary is provided in Table 5-B as follows:

TABLE 5-B

| Product Composition and Flow Rates for Example 4 | | | |
|---|---|---|---|
| Components | Feed Mass % | Raffinate (Solvent Free) Mass % | Extract (Solvent Free) Mass % |
| Mono Olefins | 35.72 | 41.57 | 0.13 |
| C6 Di-Olefins | 1.18 | 1.24 | 0.81 |
| Paraffins (Normal + Iso) | 31.54 | 36.69 | 0.13 |

TABLE 5-B-continued

Product Composition and Flow Rates for Example 4

| Components | Feed Mass % | Raffinate (Solvent Free) Mass % | Extract (Solvent Free) Mass % |
|---|---|---|---|
| Naphthenes | 17.47 | 20.35 | 0.01 |
| Aromatics (Benzene) | 14.09 | 0.14 | 98.93 |
| Total Flow Rate, Kg/hr | 70000.00 | 60118.04 | 9881.96 |
| Benzene recovery in Extract | % of Feed | | 99.12 |
| Benzene purity in Extract | Wt. % | | 98.93 |
| Benzene in Raffinate | Wt. % | 0.14 | |
| Raffinate yield | % of Feed | 85.88 | |

Results presented in Tables 5-A and 5-B indicate that when the ED columns (Col. 1 and Col. 2) are operated in vacuum at −0.285 kg/cm2g and −0.489 kg/cm2g pressures respectively; the aromatics purity in the final extract is 98.93 wt. %. The raffinate yield also increases due to lower concentration of non-aromatics in the recovered benzene. In this example, the total heating duty (17.63 MMKCal/hr) and cooling duty (19.45 MMKCal/hr) requirements are also significantly lower than the heating and cooling duty requirement of 23.76 MMKCal/hr and 25.73 MMKCal/hr respectively, of the comparative invention in U.S. Pat. No. 8,722,952 B2, as shown in previous Example 2.

The benzene purity in the extract product and the raffinate yield has also increased slightly as compared to the results shown in Example 2.

Example 5

ED Run with NMP (With side reboiler at Stage 40 in Col. 1)
  ED Column (Col.1) operating pressure (−0.285 Kg/cm2g)
  Feed: Benzene concentrated unprocessed catalytically cracked gasoline fraction (boiling in the range 48° C.-91.8° C.) as described in Table 1 (90% vaporization at 0.5 kg/cm2g)
  Solvent System: Pure NMP
  Solvent Entry Temperature in Col. 1: 90° C.
  Process Flow Scheme as in FIG. 2
  Solvent System to Feed Wt. Ratio: 4
  ED Column/Solvent Recovery Column Stage Efficiency—0.50

Individual Column operating parameters are provided in Table 6-A as follows:

TABLE 6-A

Column Operating Parameters for Example 5 (Refer FIG. 1)

| Parameters | UOM | EDC-1 (C-01) | EDC-2 (C-02) | SRC (C-03) |
|---|---|---|---|---|
| Total Number of Stages | Actual | 50 | 20 | 40 |
| Stage Efficiency assumed | | 0.5 | 0.5 | 0.5 |
| Main Feed Stage Location | | 36 | 10 | 20 |
| Column Top Pressure | Kg/cm2g | −0.285 | −0.489 | −0.517 |
| Reboiler Temperature | ° C. | 174.95 | 74.48 | 181.90 |
| Reboiler Duty (1) | MMKCal/hr | 8.692 | 0.645* | 5.465 |
| Overhead Condenser Duty (2) | MMKCal/hr | 1.214 | 6.296 | 4.988 |
| Column Reflux Rate (If any) | TPH | 6.00 | 12.01 | 37.06 |
| Column Side Reboiler Duty (If any) | MMKCal/hr | 3.5 | — | — |
| Stripping Steam Required (If any) | TPH | — | — | — |
| Feed Pre-heater duty | MMKCal/hr | | 4.835 | |
| Circulating Solvent Cooler Duty (3) | MMKCal/hr | | 3.489 | |
| Total Heating Duty Required Σ(1) except* | MMKCal/hr | | 14.16 | |
| Total Cooling Duty Required Σ(2) + (3) | MMKCal/hr | | 15.99 | |

Product summary is provided in Table 6-B as follows:

TABLE 6-B

Product Composition and Flow Rates for Example 5

| Components | Feed Mass % | Raffinate (Solvent Free) Mass % | Extract (Solvent Free) Mass % |
|---|---|---|---|
| Mono Olefins | 35.72 | 41.62 | 0.20 |
| C6 Di-Olefins | 1.18 | 1.16 | 1.31 |
| Paraffins (Normal + Iso) | 31.54 | 36.70 | 0.41 |
| Naphthenes | 17.47 | 20.38 | 0.01 |
| Aromatics (Benzene) | 14.09 | 0.14 | 98.08 |
| Total Flow Rate, Kg/hr | 70000.00 | 60031.88 | 9968.12 |
| Benzene recovery in Extract | % of Feed | | 99.12 |
| Benzene purity in Extract | Wt. % | | 98.08 |
| Benzene in Raffinate | Wt. % | 0.14 | |
| Raffinate yield | % of Feed | 85.76 | |

Results presented in Tables 6-A and 6-B indicate that when the ED columns (Col. 1 and Col. 2) are operated in vacuum at −0.285 kg/cm2g and −0.489 kg/cm2g pressures respectively even in presence of a side reboiler in Col. 1; the aromatics purity in the final extract can be obtained up to 98.00 wt. %, the rest being non-aromatic hydrocarbons. The raffinate yield is also high (>85%). The total heating and cooling duty requirements have lowered (14.16 and 15.99 MMKCal/hr respectively) in this case, due to utilization of the circulating solvent heat. A substantial amount of heat (3.5 MMKCal/hr) present in the hot circulating solvent is utilized in a side reboiler attached with the main ED Column (Col. 1) which not only decreases the column's heat load but also the cooling load of the circulating solvent cooler. The purity of the extract has decreased a bit from 98.93 wt. % to 98.08% as in Example 4. This is probably due to dissolution of more non-aromatics in the down flowing solvent (in Col. 1) on account of additional heat source from the ED Column side reboiler. Moreover, the Benzene purity in extract can be easily increased to the desired level by fine tuning the column operating parameters.

Example 6

ED Run with NMP (With side reboiler at Stage 40 in Col. 1)
  ED Column (Col.1) operating pressure (−0.285 Kg/cm2g)
  Feed: Benzene concentrated unprocessed catalytically cracked gasoline fraction (boiling in the range 48° C.-91.8° C.) as described in Table 1 (90% vaporization at 0.5 kg/cm2g)
  Solvent System: Pure NMP
  Solvent Entry Temperature in Col. 1: 70° C.
  Process Flow Scheme as in FIG. 2
  Solvent System to Feed Wt. Ratio: 4
  ED Column/Solvent Recovery Column Stage Efficiency—0.50

Individual Column operating parameters are provided in Table 7-A as follows:

TABLE 7-A

Column Operating Parameters for Example 6 (Refer FIG. 1)

| Parameters | UOM | EDC-1 (C-01) | EDC-2 (C-02) | SRC (C-03) |
|---|---|---|---|---|
| Total Number of Stages | Actual | 50 | 20 | 40 |
| Stage Efficiency assumed | | 0.5 | 0.5 | 0.5 |
| Main Feed Stage Location | | 36 | 10 | 20 |
| Column Top Pressure | Kg/cm2g | −0.285 | −0.489 | −0.517 |
| Reboiler Temperature | ° C. | 175.25 | 66.96 | 181.90 |
| Reboiler Duty (1) | MMKCal/hr | 10.578 | 0.318* | 5.366 |
| Overhead Condenser Duty (2) | MMKCal/hr | 0.383 | 6.314 | 4.918 |
| Column Reflux Rate (If any) | TPH | 6.00 | 12.04 | 37.31 |
| Column Side Reboiler Duty (If any) | MMKCal/hr | 3.5 | — | — |
| Stripping Steam Required (If any) | TPH | — | — | — |
| Feed Pre-heater duty | MMKCal/hr | 4.835 | | |
| Circulating Solvent Cooler Duty (3) | MMKCal/hr | 6.159 | | |
| Total Heating Duty Required Σ(1) except* | MMKCal/hr | 15.94 | | |
| Total Cooling Duty Required Σ(2) + (3) | MMKCal/hr | 17.77 | | |

Product summary is provided in Table 7-B as follows:

TABLE 7-B

Product Composition and Flow Rates for Example 6

| Components | Feed Mass % | Raffinate (Solvent Free) Mass % | Extract (Solvent Free) Mass % |
|---|---|---|---|
| Mono Olefins | 35.72 | 41.54 | 0.04 |
| C6 Di-Olefins | 1.18 | 1.31 | 0.36 |
| Paraffins (Normal + Iso) | 31.54 | 36.66 | 0.06 |
| Naphthenes | 17.47 | 20.33 | 0.00 |
| Aromatics (Benzene) | 14.09 | 0.15 | 99.54 |
| Total Flow Rate, Kg/hr | 70000.00 | 60180.73 | 9819.27 |
| Benzene recovery in Extract | % of Feed | | 99.10 |
| Benzene purity in Extract | Wt. % | | 99.54 |
| Benzene in Raffinate | Wt. % | 0.15 | |
| Raffinate yield | % of Feed | 85.97 | |

Results presented in Tables 7-A and 7-B indicate that when the ED columns (Col. 1 and Col. 2) are operated in vacuum at −0.285 kg/cm2g and −0.489 kg/cm2g pressures respectively even in presence of a side reboiler in Col. 1; the aromatics purity in the final extract can be obtained up to 99.54 wt. %, the rest being non-aromatic hydrocarbons. The raffinate yield is also high (>85%). The total heating and cooling duty requirements are 15.94 and 17.77 MMKCal/hr respectively in this case, due to utilization of the circulating solvent heat. A substantial amount of heat (3.5 MMKCal/hr) present in the hot circulating solvent is utilized in a side reboiler attached with the main ED Column (Col. 1) which not only decreases the column's heat load but also the cooling load of the circulating solvent cooler. On decreasing the solvent entry temperature from 90° C. to 70° C., the following changes are observed;

- Total cooling duty requirements increases (from 15.99 MMKCal/hr as in Example 5 to 17.77 MMKCal/hr as in this case) because the circulating solvent cooler has to cool more (70° C. instead of 90° C.)
- ED-01 reboiler duty increases (from 8.692 MMKCal/hr as in Example 5 to 10.578 MMKCal/hr as in this case) because the circulating solvent is now bringing in less energy as compared to the previous case (solvent entry temperature is 70° C. instead of 90° C.)
- For the same raffinate impurity content (~0.14 wt. % benzene) the purity of the extract has increases from 98.08 wt. % (as in Example 5) to 99.54 wt. %

Benefits of the energy efficient and cost effective (vacuum based extractive distillation) improved process To evaluate the quantitative benefits of the current invention over the previous process disclosed in U.S. Pat. No. 8,722,952 B2, the major parameters of Examples 2, 4, 5, and 6 are given in Table 8:

TABLE 8

Comparative result summary of the main simulation cases

| Parameters | Base case U.S. Pat. No. 8,722,952B2 Example-2 | Present Invention Example-4 | Present Invention Example-5 | Present Invention Example-6 |
|---|---|---|---|---|
| Solvent System | Aq. NMP | Pure NMP | Pure NMP | Pure NMP |
| Total No. of Columns | 4 | 3 | 3 | 3 |
| Heat Utilized in Main ED Col. Side Reboiler (MMKCal/hr) | 1.0 | — | 3.5 | 3.5 |
| Solvent Entry Temperature in main ED column (° C.) | 60.0 | 90.0 | 90.0 | 70.0 |
| Yield of Raffinate (% of feed) | 85.77 | 85.88 | 85.76 | 85.97 |
| Benzene Purity in Final Extract (wt. %) | 98.00 | 98.93 | 99.12 | 99.54 |
| Total Heating duty requirement, MMKcal/hr | 23.76 | 17.63 | 14.16 | 15.94 |
| Total Cooling duty requirement, MMKcal/hr | 25.73 | 19.45 | 15.99 | 17.77 |

It is clear from the results in the above table that with this new improved process scheme there is not only significant scope of energy savings (~33% reduction in heating and ~31% reduction in cooling duties) but also higher product yields and purities.

ADVANTAGES OF THE INVENTION

The invention provides the following advantages:
1. Simultaneous production of benzene lean gasoline and recovery of high purity aromatics from narrow boiling light cracked gasoline fractions.
2. Two stage extractive distillation process, with pure NMP, for production of benzene lean gasoline.
3. Yield and purities from the cracked gasoline feed are obtained using two coupled extractive distillation columns.
4. An energy efficient process with more than 33% heating utility savings and more than 30% cold utility savings.

It is understood that the examples and embodiments described herein are for illustrative purposes only. Unless clearly excluded by the context, all embodiments disclosed for one aspect of the disclosure can be combined with embodiments disclosed for other aspects of the disclosure, in any suitable combination. It will be apparent to those skilled in the art that various modifications and variations can be made to the subject matter of the disclosure without departing from the scope of the disclosure. Thus, it is intended that modifications and variations of the disclosure are covered provided they come within the scope of the appended claims and their equivalents.

What is claimed is:

1. A vacuum based extractive distillation process for simultaneous production of high purity benzene (>99 wt. %) and benzene lean gasoline (benzene content <0.2 wt. %) from cracked gasoline fraction, comprising the steps of:
   a) combining in an extractive distillation column (EDC-1) operating in vacuum/negative pressure (pressure below normal atmospheric pressure)
      i) a feed material comprising a preheated (upto 90% vaporization in a pressure range of −0.307 kg/cm2g to −0.247 kg/cm2g) unprocessed cracked gasoline fraction (boiling in the range of ° C. 40-90° C.) consisting of benzene concentrated unprocessed catalytically cracked gasoline fraction obtained from a fluidized catalytic cracking unit without any pretreatment, wherein the gasoline fraction contains 10-30 weight % benzene, 70-90 weight % non-aromatic hydrocarbons and impurities, wherein the impurities comprise one or more of metals at a level not exceeding in ppb level, 1-400 ppm oxygenates, 0.1-3 ppm chlorides, 100-700 ppm sulphur, 0.6-14 ppm nitrogen and organic peroxides at a peroxide level of 20-50 millimoles/liter; and
      ii) pure N-Methyl-2-Pyrrolidone (NMP) at a solvent to feed material weight ratio of about 2 to about 6, and wherein the feed material is introduced into the first ED column (EDC-1) below the middle section and the solvent at about 65° C.-95° C. is introduced into the column near the top section;
   b) operating the EDC-1 of step (a) under vacuum and maintaining reboiler temperature in a range of 175° C. to 185° C. to obtain vapour product from top and aromatics laden solvent rich extract from the bottom;
   c) cooling the vapor product from EDC-1 top as obtained in step (b), to a temperature in the range of 65° C.-75° C. and then taking it to the middle section of a second refluxed extractive distillation column (EDC-2);
   d) operating the EDC-2 of step (c) under vacuum/negative pressure and maintaining the EDC-2 reboiler temperature in a range of 67° C.-80° C. to recover a final dearomatized raffinate product containing gasoline having a benzene content of less than 0.2 weight % from top of EDC-2 and an extract phase containing aromatic hydrocarbons and solvent mixture from bottom of EDC-2;
   e) recycling the extract phase as obtained in step (d) to the top of EDC-1 to serve as reflux for EDC-1;
   f) separating the solvent from the extract phase as obtained in step (b) in a refluxed Solvent Recovery Column (SRC), operating under vacuum/negative pressure without using any stripping steam or water, to obtain hydrocarbon free solvent from the bottom and final benzene rich extract product from the SRC top.

2. The process as claimed in claim 1, wherein the solvent, free from hydrocarbons, obtained from the SRC bottom is recycled back to the EDC-1 after utilization of its heat in the EDC-1 side reboiler, EDC-2 reboiler and the main FCC gasoline feed pre-heater in the said order and finally cooled in the solvent cooler to about 65° C.-95° C. prior to its entry in EDC-1.

3. The process as claimed in claim 1, wherein top pressure of EDC-1, EDC-2 and SRC is maintained at a pressure of −0.39 to −0.19 kg/cm2g; −0.59 to −0.39 kg/cm2g and −0.62 to −0.42 kg/cm2g respectively.

4. The process as claimed in claim 1, wherein the weight ratio of reflux to the final dearomatized raffinate product from the EDC-2 top is 0.1:1 to 0.5:1.

5. The process as claimed in claim 1, wherein the ratio of extract phase from EDC-2 to the final dearomatized raffinate product is 0.1:1 to 0.15:1.

6. The process as claimed in claim 1, wherein the reflux ratio in the Solvent Recovery Column is in the range 3.5 to 4.5 wt./wt. and the reboiler temperature of the Solvent Recovery Column is in the range 175° C.-187° C. at the operating pressure.

7. The process as claimed in claim 1, wherein greater than 99 weight % of the benzene present in the catalytically cracked gasoline feed is recovered in the final benzene rich extract product from SRC top.

8. The process as claimed in claim 1, wherein the purity of benzene in the final benzene rich extract product obtained from the SRC top is more than 99 wt. % and benzene content of the final dearomatized raffinate product from EDC-2 top is less than 0.2 wt. %.

9. The process as claimed in claim 1, wherein less than 0.2 wt. % benzene in the final dearomatized raffinate product/benzene lean gasoline and more than 99% recovery of high purity benzene product (with purity of more than 99 wt. %) is obtained from the unprocessed cracked gasoline fraction having a boiling range of 40° C. to about 90° C., using two coupled extractive distillation columns in series operating under vacuum in conjunction with a solvent recovery column operating under vacuum without the aid of any stripping steam or water.

* * * * *